(12) United States Patent
Peng et al.

(10) Patent No.: US 9,250,217 B2
(45) Date of Patent: Feb. 2, 2016

(54) METHOD OF MEASURING THE ELECTROOSMOTIC TRANSPORT COEFFICIENT OF A PROTON EXCHANGE MEMBRANE AND DEVICE FOR IMPLEMENTING SUCH A METHOD

(75) Inventors: Zhe Peng, Grenoble (FR); Arnaud Morin, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 574 days.

(21) Appl. No.: 13/808,748

(22) PCT Filed: Jul. 7, 2011

(86) PCT No.: PCT/FR2011/051618
§ 371 (c)(1),
(2), (4) Date: Mar. 13, 2013

(87) PCT Pub. No.: WO2012/004538
PCT Pub. Date: Jan. 12, 2012

(65) Prior Publication Data
US 2013/0166222 A1      Jun. 27, 2013

(30) Foreign Application Priority Data
Jul. 8, 2010 (FR) ..................................... 10 55571

(51) Int. Cl.
*G01N 30/00* (2006.01)
*G06F 17/10* (2006.01)
*B01D 61/42* (2006.01)
*G01N 13/04* (2006.01)
*H01M 8/04* (2006.01)

(52) U.S. Cl.
CPC .............. *G01N 30/00* (2013.01); *B01D 61/427* (2013.01); *G01N 13/04* (2013.01); *G06F 17/10* (2013.01); *H01M 8/04634* (2013.01)

(58) Field of Classification Search
CPC ...................................................... G01N 30/00
USPC ............................................................ 702/22
See application file for complete search history.

(56) References Cited

U.S. PATENT DOCUMENTS

| 3,871,990 A | 3/1975 | Hadermann et al. |
| 2006/0228606 A1* | 10/2006 | Fiebig ................. H01M 8/0297 429/410 |

OTHER PUBLICATIONS

International Search Report as issued for PCT/FR2011/051618.
(Continued)

*Primary Examiner* — Bryan Bui
(74) *Attorney, Agent, or Firm* — Pillsbury Winthrop Shaw Pittman LLP

(57) ABSTRACT

A method of determining the electroosmotic transport coefficient of a proton exchange membrane, the method including creating a stream of hydrated hydrogen on either side of the membrane which is permanently controlled so that the relative humidity is almost identical on each side of the membrane at any point, thereby making it possible to minimize any back diffusion into the membrane. Furthermore, the method includes estimating the back diffusion flux into the membrane from the rate of return to equilibrium of the relative humidity starting from the moment when the current is cut off.

16 Claims, 6 Drawing Sheets

(56) References Cited

OTHER PUBLICATIONS

Braff et al.; "Electroosmotic Drag Coefficient of Proton Exchange Membranes as a Function of Relative Humidity", ECS Transaction—Proton Exchange Membrane Fuel Cells 8, PEMFC—214$^{th}$ ECS Meeting, vol. 16, No. 2, 2008, pp. 309-316, XP002624142; DOI: 10.1149/1.2981865, pp. 309-312.

Ji et al.; "A Review of Water Management in Polymer Electrolyte Membrane Fuel Cells", Energies, vol. 2, No. 4, Dec. 2009, pp. 1057-1106; XP002624143, DOI: 10.3390/en20401057, pp. 1058-1060.

Luo et al.; "Electro-osmotic drag coefficient and proton conductivity in Nafion membrane for PEMFC", International Journal of Hydrogen Energy, Elsevier Science Publishers B.V., Barking GB, vol. 35, No. 7, Apr. 1, 2010, pp. 3120-3124; XP026983580.

Ise, M., et al., "Electroosmotic drag in polymer electrolyte membranes: an electrophoretic NMR study," Solid State Ionics, vol. 125, 1999, pp. 213-223.

\* cited by examiner

METHOD OF MEASURING THE ELECTROOSMOTIC TRANSPORT COEFFICIENT OF A PROTON EXCHANGE MEMBRANE AND DEVICE FOR IMPLEMENTING SUCH A METHOD

CROSS REFERENCE TO RELATED APPLICATIONS

This application is the U.S. National Stage of PCT/FR2011/051618, filed Jul. 7, 2011, which in turn claims priority to French Patent Application No. 1055571, filed Jul. 8, 2010, the entire contents of all applications are incorporated herein by reference in their entireties.

TECHNICAL FIELD OF THE INVENTION

The present invention relates to a method of measuring the electroosmotic transport coefficient of a proton exchange membrane, as well as a device implementing such a method.

PRIOR ART

A proton exchange membrane fuel cell (PEMFC) is a device enabling chemical energy to be converted into electrical energy and heat by recombination of dihydrogen and dioxygen to form water. These fuel cells arouse more and more interest since they do not emit $CO_2$ when in operation.

In a proton exchange membrane fuel cell, the proton exchange membrane must separate the electrodes of the fuel cell from each other, prevent the passage of electrons from one electrode to another and enable the transport of protons generated during anodic oxidation to the cathode. However, the proton-conducting mode and the mobility of protons are strongly dependent on the quantity of water in the membrane. At equilibrium, under given conditions, this quantity of water in the membrane depends on the temperature and relative humidity of the gases. In addition, the quantity of water in the membrane is not homogeneous. In fact, the membrane is subject to a water quantity gradient that results from the competition between two fluxes:
  the electroosmosis flux from the anode to the cathode that is explained by the fact that when the protons traverse the membrane, they tend to drag water molecules with them,
  the back diffusion flux from the cathode to the anode that is mainly explained by the fact that the accumulation of water produced at the cathode and the water dragged by the electroosmosis flux to this electrode induces this diffusive flux.

This inhomogeneous distribution of the quantity of water in the thickness of the membrane limits the performance of the fuel cell as well as its lifespan.

In order to increase fuel cell performance and lifespan, it is necessary to optimize this water distribution, which requires a better knowledge of all phenomena connected to the transport of water in the membrane. More specifically, it is necessary to be able to study the electroosmosis and back diffusion phenomena separately, in order to be able to quantify them separately. To do so, it is particularly necessary to know the electroosmotic transport coefficient K that is defined as being the average number of water molecules dragged across the proton membrane in the absence of a water concentration gradient.

The prior art knows various methods for determining this electroosmotic transport coefficient.

Therefore, the publication entitled "Electro-osmotic drag in polymer electrolyte membranes: an electrophoretic NMR study" by M. Ise et al (Solid State Ionics 125 (1999) 213-223) proposes calculating the electroosmotic transport coefficient by applying a potential difference in the stack of membranes placed between two electrodes so that a current passes through this stack of membranes. This assembly is placed in an NMR tube containing a given quantity of water. However, these electroosmosis coefficient calculations are not accurate since the quantity of water in the NMR tube is not precisely known but is estimated by making many rough assumptions.

Therefore this method of determining the electroosmotic transport coefficient is complex to implement and is not reliable since the measurements are carried out outside of the stack, in an environment different from that in which the membrane will be when it will be in an operating fuel cell. In addition, this method requires stacking several membranes on top of each other and the presence of interfaces between the membranes interferes with the measurement. In addition, the quantity of water measured in the stack is not homogeneous so that the electroosmotic transport coefficient measured is an average coefficient and not a coefficient for a given quantity of water.

In addition, the document entitled "Electro-osmotic drag coefficient and proton conductivity in Nafion membrane for PEMFC" by Luo et Al, International Journal of Hydrogen Energy (2009) 1-5, describes the use of a proton pump that enables a flux of protons to be created in the plane of a proton exchange membrane situated between two compartments containing liquid water. The flux of protons into the plane of the membrane then drags a flux of water into the plane of the membrane. The authors of this document then measure the flux of water by measuring the difference in water levels between two capillaries, each placed in one of the compartments containing liquid water.

However, the measuring method used in this document is imprecise since an unknown water quantity gradient exists in the thickness of the membrane, in each compartment and also in the plane of the membrane between each compartment. In addition, the conditions, especially the current, used in this measuring method are very different from those that exist in an operating fuel cell, which leads to measuring inaccuracies.

In addition, the measuring methods of the prior art do not ensure that the electroosmotic transport coefficient calculated is representative of the electroosmosis flux in the membrane, and is not influenced by back diffusion phenomena.

DISCLOSURE OF THE INVENTION

The invention aims to remedy the disadvantages from the prior art by proposing a method of determining the electroosmotic transport coefficient in a proton exchange membrane of a fuel cell that is more reliable than methods from the prior art.

Another object of the invention is to propose a method that measures the electroosmotic transport coefficient in a proton exchange membrane under real conditions or conditions close to real conditions.

Another object of the invention is to propose a method of determining the electroosmotic transport coefficient in a proton exchange membrane that may be directly implemented in a fuel cell, without having to disassemble this fuel cell.

Another object of the invention is to propose a method of determining the electroosmotic transport coefficient in a proton exchange membrane that is simple, rapid and accurate.

Another object of the invention is to propose a method of determining the electroosmotic transport coefficient that is representative of the electroosmosis phenomenon only.

Another object of the invention is to propose a device that implements the method according to the invention.

To do so, a first aspect of the invention relates to a method of determining the electroosmotic transport coefficient of a proton exchange membrane, the membrane being disposed between a first compartment and a second compartment, the first and second compartments each extending on either side of the membrane, the first and second compartments each presenting an entrance and an exit, the entrance of the first compartment being situated facing the exit of the second compartment and vice-versa, the method comprising the following steps:

(i) establishment of a flux of hydrated gas in each of the compartments, the flux of hydrated gas in the first compartment being a flux of hydrated hydrogen, the flux of hydrated gas being directed, in each of the compartments, from the entrance to the exit, the flux of hydrated gas, in each of the compartments, being controlled such that, in continuous operation, the relative humidity in the entrance of at least one of the compartments is equal to the relative humidity in the exit of the other of the compartments;

(ii) establishment of a proton current through the membrane of the first compartment in the direction of the second compartment;

(iii) determination of the total flux of water that crosses the membrane, in continuous operation, from the first compartment in the direction of the second compartment by using at least one measurement of the quantity of water at the exit of the second compartment, (iv) calculation of the electroosmotic transport coefficient from the total water flux.

In this entire document, the electroosmotic transport coefficient is defined as being the average number of water molecules dragged across the proton membrane in the absence of a water concentration gradient in the membrane. The electroosmotic transport coefficient is also known as the electroosmosis coefficient.

"Hydrated gas" is understood to refer to a fluid that comprises gas molecules, for example dihydrogen or dioxygen, and water molecules.

"Hydrated hydrogen" is understood to refer to a fluid that comprises $H_2$ and $H_2O$ molecules. To obtain this flux of hydrated hydrogen, that is a mixture of hydrogen and water molecules, one may for example pass the gaseous hydrogen into an enclosure containing liquid water at a given dew point temperature. Another method to obtain this flux of hydrated hydrogen is to mix the fluxes of water vapour and dry gas with given flow rates.

The relative humidity of a medium, commonly noted $\phi$ or RH, corresponds to the ratio of the partial pressure of water vapour contained in this medium to the saturated vapour pressure (or vapour tension) at the same temperature. The relative humidity of a medium is therefore a measurement of the ratio between the water content of a medium and its maximum capacity to contain it under these conditions.

The act of sending fluxes of hydrated gas on either side of the membrane, that pass alongside the membrane in opposite directions from each other, and of controlling these hydrated gas fluxes in the entrance of each of the compartments such that the relative humidity at the entrance of at least one of the compartments is equal to the relative humidity at the exit of the other compartment, ensures that the relative humidity varies little on either side of the membrane.

Therefore, controlling the hydrated gas fluxes enables having a homogeneous water distribution on either side of the membrane, which limits the back diffusion phenomenon as much as possible. Consequently, the electroosmotic transport coefficient obtained by using the method according to the invention is truly representative of the electroosmosis phenomenon.

The method according to the invention therefore enables the electroosmotic transport coefficient to be calculated in a simple and accurate manner.

In addition, the method according to the invention is particularly advantageous since it may be directly implemented in a fuel cell, in which, instead of sending a flux of hydrogen into one of the compartments and a flux of oxygen into the other, a flux of hydrated hydrogen is sent into the first compartment and a flux of hydrated gas is sent into the second compartment. The flux of hydrated gas in the second compartment traverses the membrane in the direction opposite from the flux of hydrated hydrogen in the first compartment.

In addition, determination of the total water flux that traverses the membrane by measuring relative humidity is accurate and simple to implement and may be carried out by using apparatuses that are available on the market, directly at the exit of the fuel cell.

The method according to the invention may also present one or more of the characteristics below, considered individually or according to all technically possible combinations.

Advantageously, the flux of hydrated gas in the second compartment is also a flux of hydrated hydrogen.

Advantageously, the membrane extends along a longitudinal direction and the first and second compartments extend on either side of the membrane along the longitudinal direction.

Advantageously, the flux of hydrated gas in each of the compartments, is also controlled so that, in continuous operation, the relative humidity remains substantially the same between the entrance and the exit of each compartment.

The fluxes of hydrated gas on either side of the membrane are preferably controlled such that:
- when two points situated on either side of the membrane are chosen, the two points belonging to the same transverse plane, the relative humidity between these two points does not vary by more than five percent between these two points;
- when moving in one compartment along the longitudinal direction, the relative humidity in this compartment does not vary by more than 5% between the entrance and the exit.

"Transverse direction" is understood to refer to a direction perpendicular to the longitudinal direction.

Advantageously, the fluxes of hydrated gas are controlled so that, when placed in a transverse plane, the relative humidity is, at all points, equal on either side of the membrane.

Advantageously, the flux of hydrated gas in each of the compartments, is controlled so that, in continuous operation, the relative humidity remains substantially the same between the entrance and the exit of each compartment.

In order to ensure that the relative humidity is homogenous when moving between the entrance and the exit of a compartment, the flow rate of hydrated gas is preferably controlled by the intensity of the proton current that traverses the membrane, such that the flux of protons, and thus water, that traverses the membrane is insignificant compared to the flux of hydrated gas, and thus water, that traverses each of the compartments on either side of the membrane. This method enables having an insignificant variation in relative humidity when moving along the longitudinal direction in one of the compartments.

Therefore the flux of hydrated hydrogen is controlled such that it is very significant compared to the fluxes of protons and water that traverse the membrane.

Advantageously, the flux of hydrated gas that traverses each of the compartments is preferably between 10 times and 2000 times greater than the flux of protons that traverses the membrane. The flux of hydrated gas is preferably between 50 and 1500 times greater than the flux of protons that traverses the membrane, and preferably substantially equal to 1000 times the flux of protons that traverse the membrane.

The measurement of the quantity of water at the exit of the second compartment may be:
- a measurement of the relative humidity at the exit of the second compartment;
- a measurement of the water weight at the exit of the second compartment.

Besides, in order to ensure that two points situated on either side of the membrane present substantially the same relative humidity, two methods may be used.

According to the first method, step (i) comprises the following steps:
- sending a single flux of hydrated hydrogen to the entrance of one of the compartments such that this single flux of hydrogen traverses this compartment,
- recovery of the single flux of hydrated hydrogen at the exit of this compartment,
- sending the single flux of hydrated hydrogen recovered to the entrance of the other of the compartments.

Therefore, the first method consists of connecting the exit of one of the compartments to the entrance of the other by making a loop. In this way, the relative humidity at the entrance of one of the compartments is always equal to the relative humidity at the exit of the other of the compartments, and that the proton current in the membrane is either null or non-null. In fact, when a proton current is established in the membrane, the protons tend to drag water molecules with them. Therefore, the molecules from the first compartment tend to be dragged into the second compartment. Such being the case, as the exit of one of the compartments is connected to the entrance of the other of the compartments, the water molecules that had been dragged from the first compartment to the second compartment are returned to the first compartment via the loop, that enables having a homogeneous distribution of water between the two compartments. Therefore, there is no gradient in the membrane and therefore no back diffusion.

According to this embodiment, the flux of hydrated gas is a flux of hydrated hydrogen in the two compartments.

Advantageously, the exit of the second compartment is fluidly connected to the entrance of the first compartment. According to second method, step (i) comprises the following simultaneous steps:
- sending a flux of hydrated hydrogen to the entrance of the first compartment so that the relative humidity at the entrance of the first compartment is equal to the relative humidity at the exit of the second compartment;
- sending a flux of hydrated gas to the entrance of the second compartment so that the relative humidity at the entrance of the second compartment is equal to the relative humidity at the exit of the first compartment.

Therefore, the second method consists of measuring the relative humidity at the exit of each compartment and stabilizing the flux of hydrated gas at the entrance of each compartment at the relative humidity at the exit of the other compartment. According to this embodiment, the fluxes of hydrated gas that go into each compartment come from two different sources, but the relative humidity that they generate at the entrance of each of the compartments is identical. Therefore, the relative humidity on either side of the membrane is identical, which prevents the back diffusion phenomenon. However, this method is more complicated than the previous.

According to a preferential embodiment, step (iii) of determining the total water flux that traverses the membrane comprises the following steps:
- calculation of the flux of water sent to the entrance of one of the compartments,
- a measurement of the relative humidity at the exit of this compartment,
- calculation of the flux of water at the exit of this compartment,
- calculation of the total water flux having traversed the membrane by calculating the difference between the water flux at the entrance and at the exit of this compartment.

In fact, by differentiating between the flux of water at the entrance of a compartment, that is known, and the flux of water at the exit of this same compartment, that is equal to the flux of water at the entrance to which the water that traversed the membrane is added (or removed), the flux of water that traversed the membrane is obtained.

Advantageously, the flux of water at the exit of a compartment is calculated from the measurement of relative humidity at the exit of this compartment. The flux of water at the exit of a compartment may also be calculated from the measurement of the water weight or water volume at the exit of this compartment.

Advantageously, the flux of water at the entrance of a compartment is calculated from:
- the measurement of the flow rate of hydrated gas that is sent to the entrance of this compartment, and
- the relative humidity of the hydrogen that is known;
- the total gas pressure;
- the saturated vapour pressure of the gas, that depends on the temperature of the gas.

According to a first embodiment of the method according to the invention, during step (iv), the total water flux is preferably assimilated to an electroosmosis flux.

In fact, as a first approximation, as the differences between relative humidity on either side of the membrane have been limited as much as possible, it may be deemed that there is no back diffusion across the membrane and therefore the electroosmosis flux is substantially equal to the total water flux.

The electroosmotic transport coefficient is then calculated by considering that the electroosmosis flux is equal to the total water flux.

This embodiment of the invention presents the advantage of being very simple to implement and also relatively accurate, since in reality, the back diffusion flux is effectively very low compared to the electroosmosis flux.

According to another preferential embodiment of the method according to the invention, step (iv) comprises the following steps:
- (v) a step of calculating the back diffusion flux that traverses the membrane from the second compartment to the first compartment;
- (vi) a step of calculating the electroosmosis flux from the sum of the total water flux and the back diffusion water flux.

Therefore, this second embodiment of the invention comprises a step of estimating the back diffusion flux, which enables having a more accurate result relating to the electroosmotic transport coefficient.

In fact, even if the back diffusion flux is very low, it may be necessary to estimate it to have a more accurate result.

Step (v) of calculating the back diffusion flux preferably comprises the following steps:
- stopping the proton current through the membrane;
- recording the curve representative of the variation in relative humidity at the exit of the second compartment as a function of time;
- calculating the curve representative of the variation in water flux at the exit of the second compartment as a function of time;
- calculating the back diffusion flux by interpolation of the curve representative of the variation in water flux at the exit of the second compartment as a function of time.

In fact, the curve of the variation in relative humidity at the exit of the second compartment as a function of time and the curve of the variation in water flux at the exit of the second compartment as a function of time are equal, within a multiplying factor.

The step of calculating the back diffusion flux by interpolation preferably comprises the following steps:
- search for the function of the form $\lambda_1 e^{-t/\tau_1} + \lambda_2 e^{-t/\tau_2} + \lambda_3$ that is most similar to the curve representative of the flux of water at the exit of the second compartment as a function of time, with a first term $\lambda_1$ associated with the total water flux in which the time constant is $\tau_1$, and a second term $\tau_1$ with $\tau_2$ associated with relaxation of the water gradient due to back diffusion;
- identification of the back diffusion flux to coefficient $\lambda_2$ associated with the time constant $\iota_2$ that is higher with relation to $\tau_1$.

In fact, the back diffusion flux may be estimated from the rate of return to equilibrium of the relative humidity from the time when the flux of hydrated gas is cut. In fact, once the current is stopped, the electroosmosis flux stops very rapidly with a low characteristic time $\tau_1$ while the water gradient in the membrane takes longer for it to relax by the diffusion, which means that the back diffusion flux takes longer to disappear with a high characteristic time $\tau_2$.

Therefore, the variation in relative humidity over time and thus in the flux of water at the exit of the second compartment once the current is stopped may be represented by two first order exponentials, each defined by an amplitude and a characteristic time, with the amplitude that represents the total flux or the back diffusion flux and the characteristic time that represents the relaxation time of the total flux and the back diffusion flux after stopping the current in the membrane. By interpolating the return to equilibrium curve of relative humidity, the back diffusion flux in continuous operation corresponding to amplitude $\lambda_2$ may thus be calculated.

The electroosmosis flux is then equal to the total water flux to which the back diffusion flux is added. The electroosmotic transport coefficient is then calculated from the electroosmosis flux only.

Advantageously, the method according to the invention also comprises a step of verifying that the quantity of water in the membrane does not change during the measurement by measuring the resistance of the "first compartment-second compartment-membrane" assembly by impedance spectroscopy.

The method according to the invention therefore enables measurement of the electroosmosis coefficient under real conditions, by taking the back diffusion into consideration when a very accurate measurement is necessary, by controlling the quantity of water in the membrane, by taking a rapid measurement of the electroosmotic transport coefficient.

In addition, the method according to the invention enables study of the variation in the electroosmotic transport coefficient, particularly as a function of temperature, the quantity of water in the membrane or the current density if need be, since the method according to the invention enables several measurements to be taken under real conditions by varying the parameters such as the temperature of the membrane, the quantity of water in the membrane or the current density.

The invention also relates to a device for determining the electroosmotic transport coefficient of a proton exchange membrane by using the method according to any one of the previous claims, the device comprising the following elements:
- a first and a second compartment (2, 3) extending on either side of the membrane (1), the first and the second compartments each comprising an entrance (10, 11) and an exit (12, 13), the entrance (10) of the first compartment (2) being situated opposite from the exit (13) of the second compartment (3) and vice-versa,
- at least one hydrated gas supply (8, 20, 27) capable of sending a flux of hydrated hydrogen to the entrance (10) of the first compartment (2) and a flux of hydrated gas (3) to the entrance (11) of the second compartment (3),
- a power supply (16) capable of establishing a proton current across the membrane (1) from the first compartment (2) to the second compartment (3),
- means (22) for measuring the quantity of water at the exit of the second compartment,
- means for measuring and controlling the flow rate (19, 26) of the hydrated gas supply at the entrance of the second compartment,
- a computer able to implement the steps of the method according to any one of the embodiments of the invention.

The device according to the invention may also present one or more of the characteristics below, considered individually or according to all technically possible combinations.

Advantageously, the device according to the invention also comprises a looping system that connects the exit of the second compartment to the entrance of the first compartment.

Advantageously, the first compartment comprises an anode disposed against the membrane and a channel disposed against the anode in which the hydrated gas flux may flow.

Advantageously, the second compartment comprises a cathode disposed against the membrane and a channel disposed against the cathode in which the hydrated gas flux may flow.

Advantageously, the means for measuring the relative humidity are able to measure the relative humidity with an accuracy of +/−0.1% and with a time resolution of less than a second. This type of sensor is commercially available.

According to another embodiment, the relative humidity may also be calculated by measuring the ultrasound wave propagation speed in the medium in which one wishes to know the relative humidity. This enables the necessary accuracy and time resolution.

Advantageously, the membrane extends along a longitudinal direction.

BRIEF DESCRIPTION OF THE FIGURES

Other characteristics and advantages of the invention will emerge upon reading the following description, with reference to the attached figures, that illustrates.

For more clarity, identical or similar elements are marked by identical reference signs on all of the figures.

DETAILED DESCRIPTION OF ONE EMBODIMENT

Figure 1:
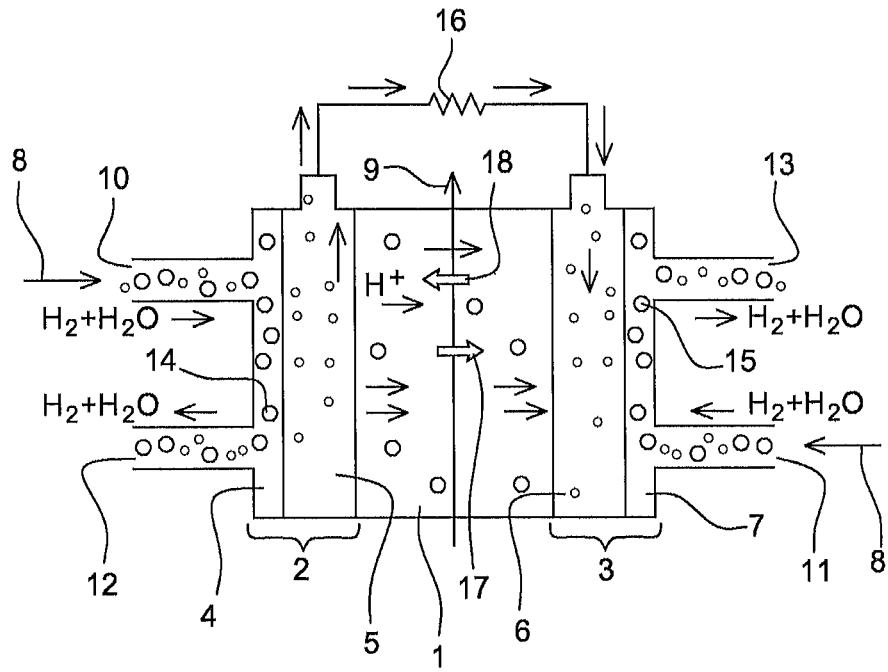
FIG. 1, a cross sectional schematic representation of a fuel cell in which the method according to the invention is implemented, FIG. 2, a cross sectional schematic representation of a device implementing the method according to the invention, FIG. 3, a cross sectional schematic representation of a device implementing a method according to a first embodiment of the invention, FIG. 4, a cross sectional schematic representation of a device implementing a method according to a second embodiment of the invention, FIG. 5, a curve representing the variation in relative humidity as a function of the time enabling the back diffusion flux in the membrane to be estimated from any one of the previous figures, FIG. 6, a curve representing the results obtained for the electroosmotic transport coefficient by the method according to the invention as a function of the relative humidity of the cell, FIG. 7, a curve representing the results obtained for the electroosmotic transport coefficient by the method according to the invention as a function of the quantity of water in the membrane, FIG. 8, the steps of a method according to the invention.

FIG. 1 represents a single fuel cell in which the method according to the invention is implemented.

Figure 2:
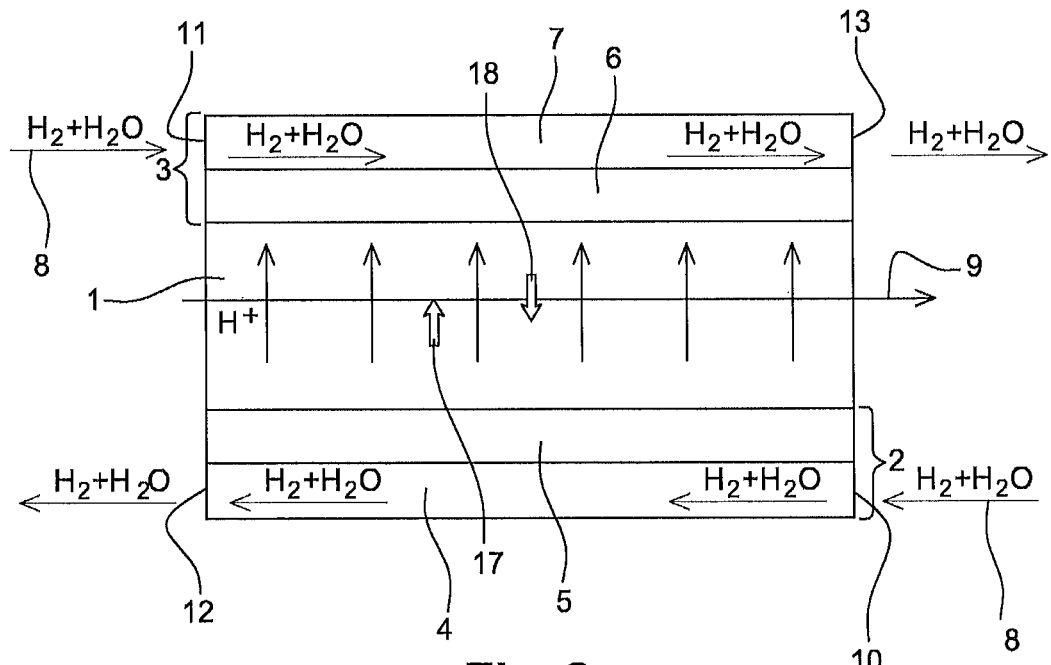

FIG. 2 represents a device in which the method according to the invention is implemented.

In the case of FIG. 1, as in the case of FIG. 2, one wishes is to measure the electroosmotic transport coefficient K of a proton exchange membrane 1.

To do so, membrane 1 is disposed between a first compartment 2 and a second compartment 3. The first compartment 2 comprises a first channel 4 in which the chemical species may circulate and an anode 5. The second compartment 3 comprises a second channel 7 in which the chemical species may circulate and a cathode 6.

The membrane extends along a longitudinal direction 9. The first and second channels each extend on either side of the membrane along the longitudinal direction 9.

The first and second channels 4, 7 each comprise an entrance, respectively 10, 11, and an exit, respectively 12, 13. The entrance of each channel is situated at the level of one end of the membrane and the exit of each channel is situated at the level of one end of the membrane.

The entrance 10 of the first channel is situated opposite from exit 13 of the second channel and entrance 11 of the second channel is situated opposite from exit 12 of the first channel.

The devices enabling implementation of the method according to the invention also comprise at least one hydrated hydrogen supply 8 capable of sending a flux of hydrated hydrogen, the flow rate of which is controlled in each of the channels.

Therefore, due to the disposition of channels along the membrane, the flux of hydrated hydrogen 14 in the first channel 4 passes alongside the membrane in the direction opposite from the flux of hydrated hydrogen 15 that traverses the second channel 7.

The device enabling implementation of the method according to the invention also comprises a power supply 16 that connects the anode 5 to the cathode 6 and that establishes an electrical current between the anode and the cathode that leads to reestablishment of a proton current $H^+$ in membrane 1. This proton current traverses the membrane from the first compartment in the direction of the second compartment.

One may also consider reversing the current and in this case, the anode would become the cathode and vice-versa.

The protons $H^+$ that traverse the membrane drag water molecules with them, which creates an electroosmosis flux 17 from the first compartment to the second compartment.

In order to better understand the behaviour of the membrane, it is advantageous to be able to study the electroosmosis phenomenon and the back diffusion phenomenon separately. To do so, knowledge of the electroosmotic transport coefficient is necessary.

The electroosmotic transport coefficient K is given by the following formula:

$$K = \phi_{electroosmosis}/\phi_{H^+}$$

Where $\phi_{electroosmosis}$ is the electroosmosis flux; the electroosmosis flux may also be defined as being the flux of water imposed by the flux of protons that traverse the membrane;

$\phi_{H}^+$ is the flux of protons that traverse the membrane.

The flux of protons that traverse the membrane $\phi_{H}^+$ depends on the current applied between the anode and the cathode and the prior art knows various methods for accurately calculating this proton flux that traverses the membrane, knowing the current applied between the anode and the cathode.

The method according to the invention is particularly remarkable in that it enables the electroosmosis flux $\phi_{electroosmosis}$ to be determined with accuracy.

To do so, the method according to the invention first of all proposes:

measuring the total water flux that traverses the membrane and is the resultant of the electroosmosis flux and the back diffusion flux, minimizing the back diffusion flux so as to make it insignificant, such that the total water flux is substantially equal to the back diffusion flux.

The steps of the method according to the invention enabling the back diffusion flux in the membrane to be minimized will now be described in further detail with reference to FIGS. 3 and 4.

In fact, to minimize the back diffusion flux, the method according to the invention first of all proposes controlling the hydrated hydrogen flux at the entrance of each of the compartments such that the relative humidity in the "first and second compartment-membrane" assembly is homogeneous.

More precisely, the method according to the invention proposes controlling the hydrated hydrogen fluxes at the entrance of at least one of the compartments such that:

the relative humidity remains substantially the same along each compartment when moving along the longitudinal direction;

the relative humidity at entrance 10 of the first compartment is equal to the relative humidity at exit 13 of the second compartment. In this way, the relative humidity remains substantially the same on either side of the membrane.

In order to ensure that the relative humidity remains substantially the same along each compartment when moving along the longitudinal direction, the method according to the invention proposes choosing the hydrated hydrogen fluxes at the entrance of each of the compartments such that the relative humidity, i.e., the water concentration, varies little between the entrance and the exit of each compartment, whatever the current, by imposing hydrated hydrogen fluxes 14, 15 that are greater than water fluxes 17, 18 that traverse the membrane.

To do this, the hydrated hydrogen fluxes at the entrance of each of the compartments are preferably chosen such that they are 1000 times greater than the flux of protons that traverse the membrane.

Therefore, the local water concentration is very homogeneous in each of the compartments:

$$HR_1^{entrance} = HR_1^{exit} + \Delta HR_1 \text{ and}$$

$$HR_2^{entrance} = HR_2^{exit} + \Delta HR_2.$$

With $HR_1^{entrance}$ that represents the relative humidity in the entrance of the first compartment, $HR_1^{exit}$ that represents the relative humidity in the exit of the first compartment, $HR_2^{entrance}$ that represents the relative humidity at the entrance of the second compartment, $HR_2^{exit}$ that represents the relative humidity at the exit of the first compartment, $\Delta HR_1$ that is between $]0; 5\%]$ of $HR_1^{entrance}$ and $\Delta HR_2$ that is between $]0; 5\%]$ of $HR_2^{entrance}$.

In this way, the relative humidity is relatively homogeneous along the longitudinal direction and therefore there is not a very low water concentration gradient along the longitudinal direction.

In addition, in order to ensure that the relative humidity of one side of the membrane is equal to the relative humidity of the other side of the membrane, the method according to the invention proposes:

either regulating the relative humidity at the entrance of one of the compartments so that it is either identical to that of the exit of the other compartment by a measurement when the current is null and a measurement when the current is non-null. In this case, the flux of hydrated hydrogen that supplies each of the compartments comes from two different sources, the flow rates of which are regulated independently from each other but in which the relative humidity levels are connected; this is the first method of regulating the fluxes that may be used by the method according to the invention;

or connecting the exit of one of the compartments to the entrance of the other by making a loop. With this configuration, the relative humidity levels in the two compartments are directly connected. Thanks to the loop, the relative humidity at the entrance of one of the compartments is always identical to that of the exit of the other compartment, as the current is null or non-null. This latter method is much simpler to implement and requires less equipment; this is the second method of regulating the fluxes that may be used by the method according to the invention.

Figure 3:
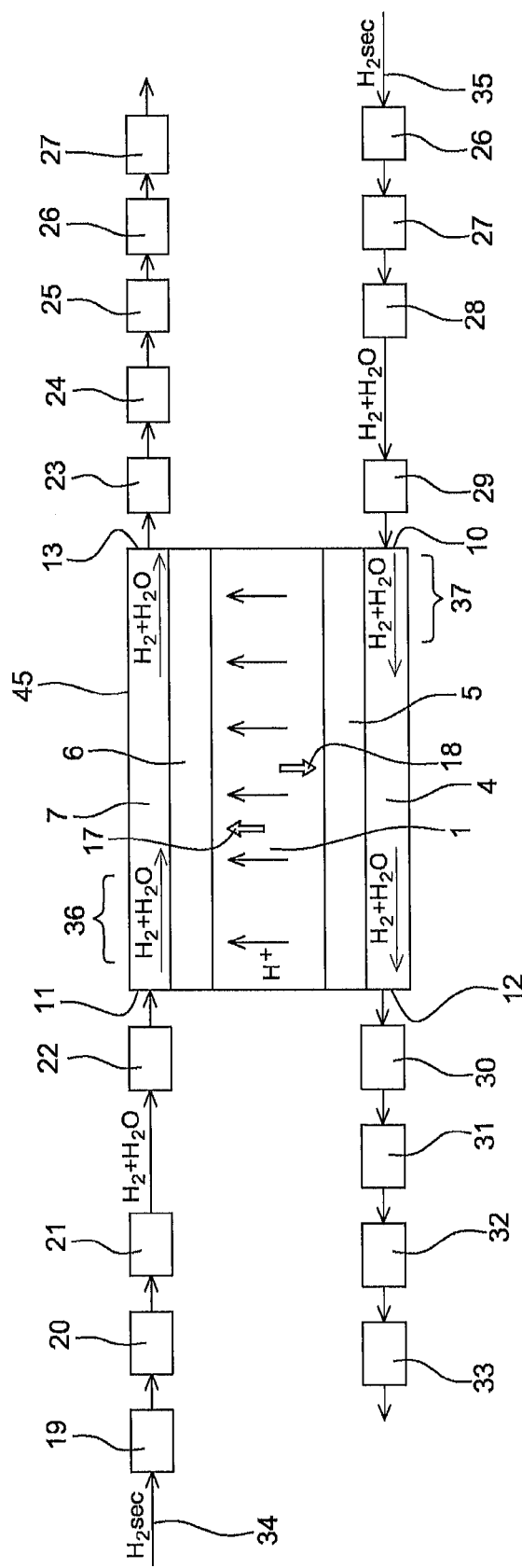

FIG. 3 schematically represents a device that implements a method according to the invention that uses the first method of regulating the flux of hydrated hydrogen.

The device from FIG. 3 comprises, at entrance 11 of the second compartment, respectively at entrance 10 of the first compartment:
- a dry hydrogen supply 34, 35,
- means for controlling the hydrogen flow rate 19, 26,
- a pressure sensor 20, 27,
- a humidifier 21, 28 that enables the dry hydrogen issued from the hydrogen supply to be transformed into hydrated hydrogen,
- means for measuring the relative humidity 22, 29 at the entrance of the second compartment (respectively the first compartment), The device from FIG. 3 also comprises, at the level of the cell, a temperature sensor 45 capable of measuring the temperature of the cell $T_{cell}$.

The device from FIG. 3 also comprises at the exit 13 of the second compartment a sensor 23 capable of very accurately measuring the relative humidity at the exit 13 of the second compartment.

Preferably, sensor 23 is able to measure the relative humidity with an accuracy of +/−0.1% with a time resolution of less than a second.

In addition, the device from FIG. 3 preferably comprises, at entrance 13 of the second compartment (respectively at entrance 12 of the first compartment):
- a phase separator 24, 30,
- a condenser 25, 31,
- a pressure sensor 26, 32,
- a pressure regulator 27, 33.

According to this embodiment of the invention, the fluxes of hydrated hydrogen 36 and 37 at the entrance of the second and first compartments are independent, but the relative humidity at exit 13 of the second compartment is continuously measured thanks to sensor 23 and the flux of hydrated hydrogen 37 injected at entrance 10 of the first compartment is controlled, thanks to the relative humidity measurement means 29, such that the relative humidity at entrance 10 of the first compartment is equal to the relative humidity measured at exit 13 of the second compartment.

However, this embodiment is relatively complicated to implement.

Figure 4:
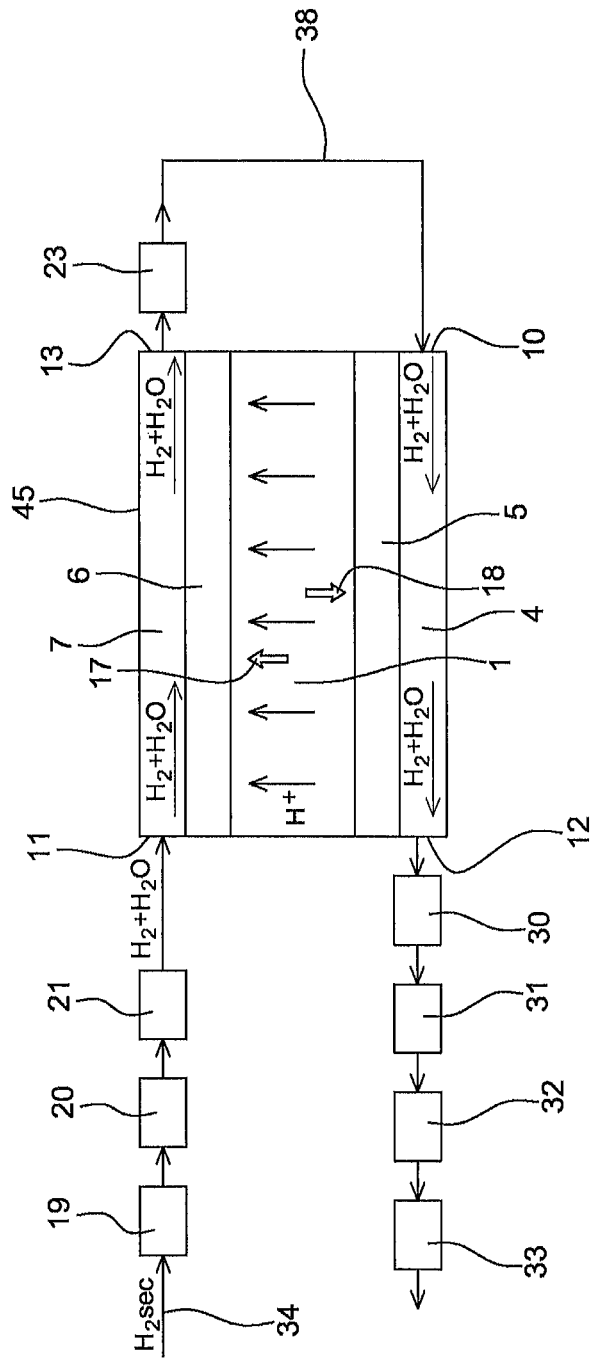
Figure 5:
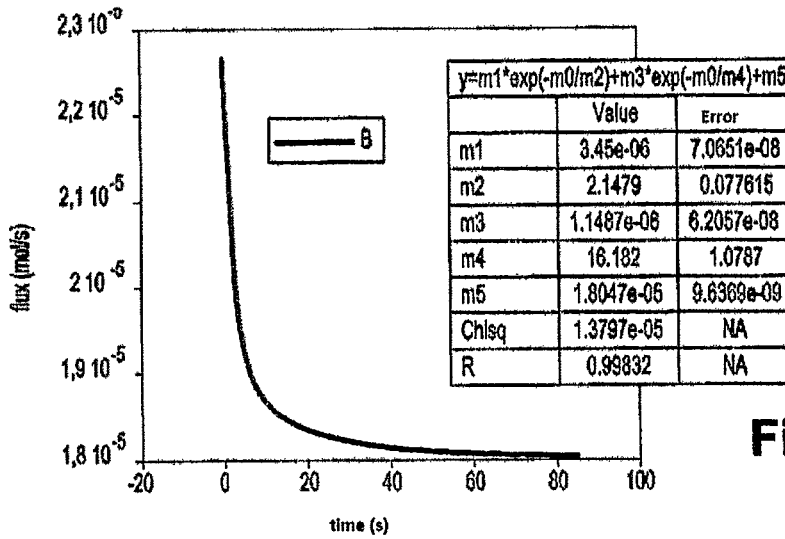

FIG. 4 schematically represents a device that implements a method according to the invention that uses the second method of regulating the flux of hydrated hydrogen.

This device is much simpler than the device from FIG. 3 since it only comprises, at entrance 11 of the second compartment:
- a dry hydrogen supply 34,
- means for controlling the dry hydrogen flow rate 19,
- a pressure sensor 20,
- a humidifier 21 that enables the dry hydrogen issued from the hydrogen supply to be transformed into hydrated hydrogen.

The device from FIG. 4 also comprises, at the level of the cell, a temperature sensor 45 capable of measuring the temperature of the cell $T_{cell}$.

The device from FIG. 4 also comprises at the exit 13 of the second compartment a sensor 23 capable of very accurately measuring the relative humidity at the exit 13 of the second compartment.

In addition, the device from FIG. 4 comprises connection means 38 that allow fluid communication between exit 13 of the second compartment and entrance 10 of the first compartment such that the relative humidity at entrance 10 of the first compartment is equal to the relative humidity at exit 13 of the second compartment.

The device from FIG. 4 also comprises at exit 12 of the first compartment;
- a phase separator 30,
- a condenser 31,
- a pressure sensor 32
- a pressure regulator 33.

Figure 8:
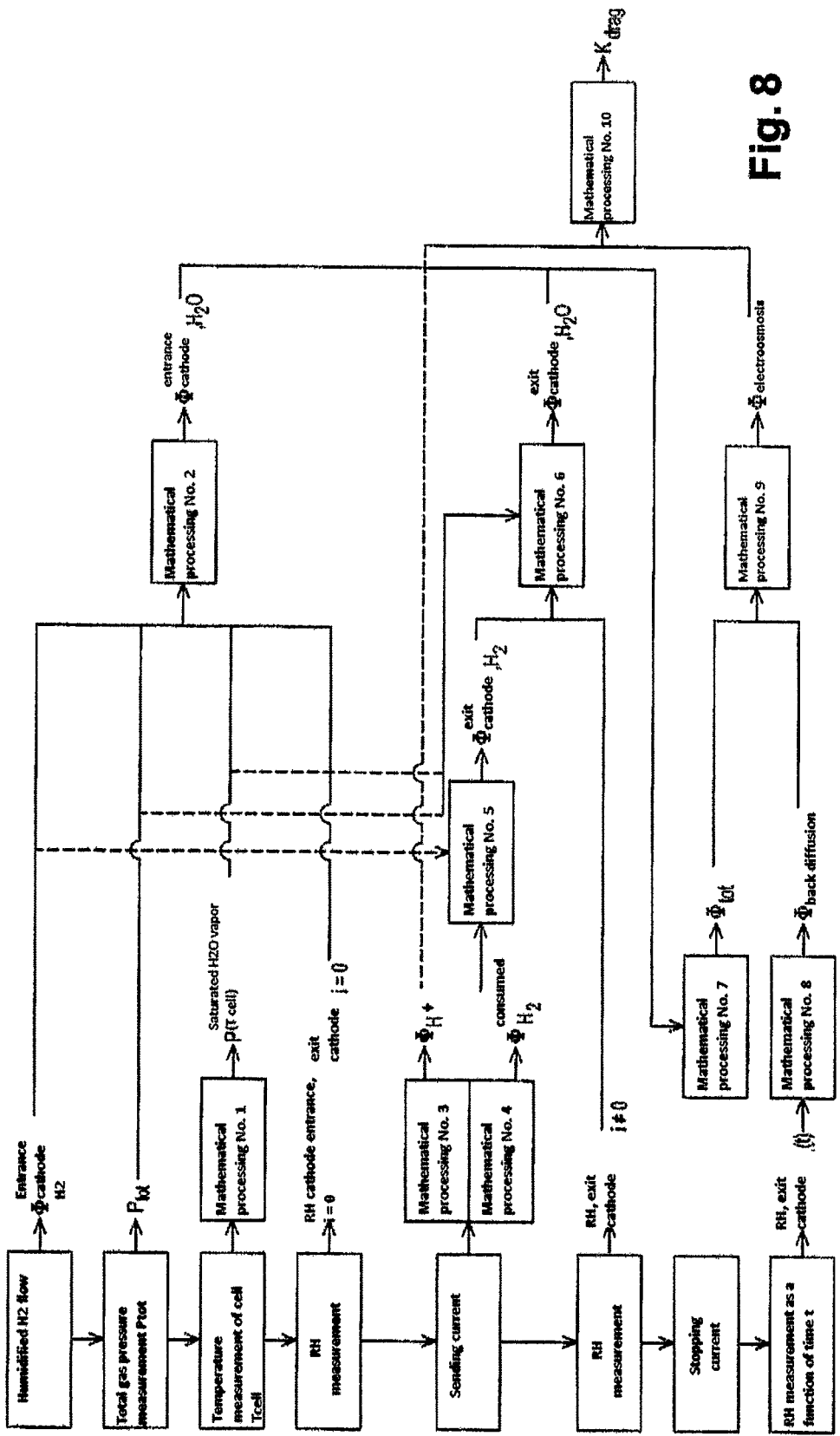

The steps of calculating the electroosmotic coefficient used by the method according to the invention implemented by the device from FIG. 4 are now explained in further detail with reference to FIG. 8. The person skilled in the art could easily adapt these steps to implement the method according to the invention implemented by the device from FIG. 3.

In the following, the "membrane-first compartment-second compartment" assembly is referred to as a "cell."

The method according to this embodiment first of all comprises a step of measuring the flux of hydrated hydrogen at entrance 11 of the second compartment. Measuring the flux of hydrated hydrogen at entrance 11 of the second compartment enables the hydrogen flux $\phi_{2,H_2}^{entrance}$ that is sent to entrance 11 of the second compartment to be calculated.

The method then comprises a measurement of the total pressure of the saturated hydrogen $P_{tot}$ as well as the temperature of the cell $T_{cell}$.

The method then comprises a step of calculating the saturated water vapour pressure vapor pressure $P_{vaporH_2O}^{saturated}(T_{cell})$ at this temperature thanks to the following formula (mathematical processing No. 1):

$$P_{vaporH_2O}^{saturated}(T_{cell}) = 10^{29,8605 - \frac{3152,2}{T_{cell}} - 7,3037 \log_{10} T_{cell} + 2,42 \cdot 10^{-9} \times T_{cell} + 1,81 \cdot 10^{-6} \times T_{cell}^2}$$

The method then comprises a step of measuring the relative humidity at the exit of the second compartment in the absence of current in the device $HR_{2,i=0}^{exit}$.

Such being the case, there is no current, the flux of water remains the same everywhere, and therefore the relative humidity at the exit of the first compartment is equal to the relative humidity at the entrance of the second compartment:

$$HR_{2,i=0}^{entrance} = HR_{1,i=0}^{exit}$$

These data then enable the flux of water at the entrance of the second compartment $\phi_{2,H_2O}^{entrance}$ to be calculated thanks to the following formula (mathematical processing No. 2):

$$HR_{2,i=0}^{entrance} = \frac{\phi_{2,H_2O}^{entrance}}{\phi_{2,H_2O}^{entrance} + \phi_{2,H_2}^{entrance}} * \frac{P_{tot}}{P_{vaporH_2O}^{saturated}(T_{cell})}$$

$$\Rightarrow \phi_{2,H_2O}^{entrance} = \frac{HR_{2,i=0}^{entrance}}{\frac{P_{tot}}{P_{vaporH_2O}^{saturated}(T_{cell})} - HR_{2,i=0}^{entrance}} * \phi_{cathode,H_2}^{entrance}$$

$\phi_{2,H_2O}^{entrance}$ is therefore the flux of water entering in the system when no current is applied to it.

Until here no current was applied between the anode and the cathode.

A current is then established between the anode and the cathode so as to create a current of protons across the membrane.

Knowing the current I applied by the electrical power supply 16 that connects the anode 5 to the cathode 6, the flux of protons may be calculated thanks to the following formula (mathematical processing No. 3):

$$\phi_{H^+} = \frac{I}{N_A * e^-}$$

With: $N_A$: Avogadro's number $6.023 \times 10^{23}$ mol$^{-1}$
$e^-$: Elementary charge $1.6 \times 10^{19}$ C In addition, as there is the proton reduction ($2H^+ + 2e^- \rightarrow H_2$) at the cathode, there is a quantity of additional hydrogen created that is added to the flux of hydrated hydrogen at the exit of the cathode (resp. consumed at the anode), which may then be calculated from the current sent thanks to the following formula:

$$\phi_{H_2}^{consumed} = \frac{I}{2 * N_A * e^-}$$

(mathematical processing No. 4).

The method then comprises a step of calculating the total hydrogen flux at the exit of the cathode thanks to the following formula:

$$\phi_{2,H_2}^{exit} = \phi_{2,H_2}^{entrance} + \phi_{H_2}^{consumed} \quad \text{(mathematical processing No. 5).}$$

The method then comprises a step of calculating the flux of water at the exit of the cathode $\phi_{2,H_2O}^{exit}$ (mathematical processing No. 6).

In fact, when the protons traverse the membrane, water is brought from the first compartment to the second compartment by the protons and therefore, when moving in the second compartment along the longitudinal direction, from the entrance to the exit, the relative humidity value will increase.

The current between the anode and the cathode must be maintained for a sufficiently long period so that the system again reaches an equilibrium mode.

The value of the relative humidity at equilibrium $HR_{2,i\neq0}^{exit}$ in the presence of a current then enables the flux of water at the exit of the second compartment $\phi_{2,H_2O}^{exit}$ to be calculated thanks to the following formula:

$$HR_{2,i\neq0}^{exit} = \frac{\phi_{2,H_2O}^{exit}}{\phi_{2,H_2O}^{exit} + \phi_{2,H_2}^{exit}} * \frac{P_{tot}}{P_{vaporH_2O}^{saturated}(T_{cell})}$$

$$\Rightarrow \phi_{2,H_2O}^{exit} = \frac{HR_{2,i=0}^{exit}}{\frac{P_{tot}}{P_{vaporH_2O}^{saturated}(T_{cell})} - HR_{2,i\neq0}^{exit}} * \phi_{2,H_2}^{exit}$$

The method then comprises a step of calculating the total water flux $\phi_{total}$ that that traverses the membrane from the first compartment to the second compartment when a current is established between the anode and the cathode thanks to the following formula:

$$\phi_{total} = \phi_{2,H_2O}^{exit} - \phi_{2,H_2O}^{entrance} \quad \text{(mathematical processing No. 7).}$$

The method according to the invention then comprises, preferably, a step of calculating the back diffusion flux that traverses the membrane from the second compartment to the first compartment (mathematical processing No, 8), due to the presence of a local water concentration gradient between each surface of the membrane of each compartment, due to the restriction on the transport of gases in the first and second compartments, due to the presence of electrodes.

To calculate this back diffusion flux, the method according to the invention proposes stopping the current between the anode and the cathode and measuring the variation in relative humidity at the exit of the cathode $HR_2^{exit}(t)$ as a function of the time from the moment when the current is cut off.

This relative humidity $HR_2^{exit}(t)$ is then converted into a water flux.

Figure 6:
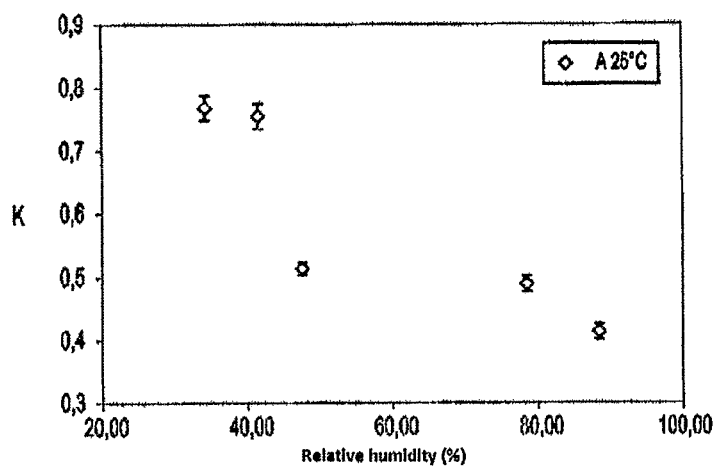

FIG. 6 represents the water flux variation curve as a function of time. This curve is then interpolated. In fact, one seeks the function of the form $\lambda_1 e^{-t/\tau_1} + \lambda_2 e^{-t/\tau_2} + \lambda_3$ that is most similar to this curve. The back diffusion flux $\phi_{retrodiffusion}$ is then equal to the coefficient $\lambda_1$ or $\lambda_2$ associated with the highest time constant $\tau_1$ or $\tau_2$.

The method then comprises a step of calculating the electroosmosis flux $\alpha_{electroosmosis}$ thanks to the following formula (mathematical processing No. 9).

$$\phi_{electroosmosis} = \phi_{total} + \phi_{backdiffusion}$$

Lastly, the method according to the invention comprises a step of calculating the electroosmotic transport coefficient $K_{drag}$, thanks to the following formula (mathematical treatment No. 10):

$$K_{drag} = \frac{\phi_{electroosmotic}}{\phi_{H+}}$$

The method such as previously described may be carried out by sending at the entrance of the second compartment fluxes of hydrated hydrogen presenting relative humidity in order to be able to study the variation in the electroosmotic transport coefficient as a function of the relative humidity in the cell. The results obtained by the method according to the invention for the coefficient K for various relative humidity values, at a temperature of 25° C., are given in FIG. 6.

Figure 7:
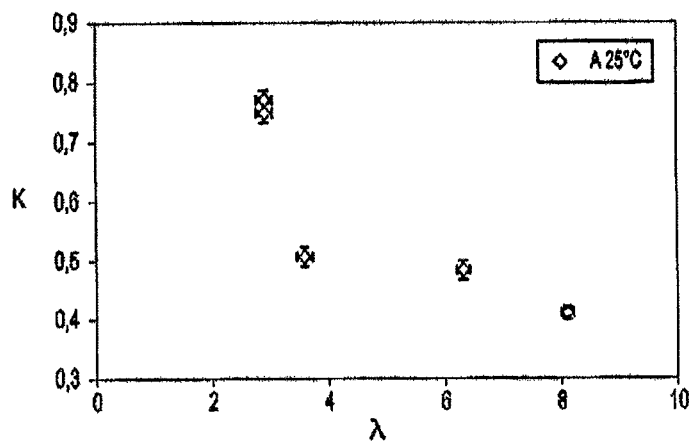

In addition, by using measured sorption isotherms, giving the relationship between the quantity of water in the membrane and the relative humidity in the cell, it is possible, thanks to the method according to the invention, to know the electroosmotic transport coefficient K as a function of the quantity of water and the temperature. The results obtained by the method according to the invention are represented in FIG. 7.

Naturally, the invention is not limited to the embodiments described with reference to the figures and variations may be contemplated without departing from the scope of the present invention.

Figure 9:
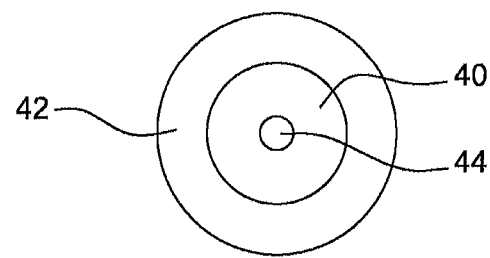
FIG. 9, a top view of another device implementing the method according to the invention, FIG. 10, a cross sectional view of the device from FIG. 9.
Figure 10:
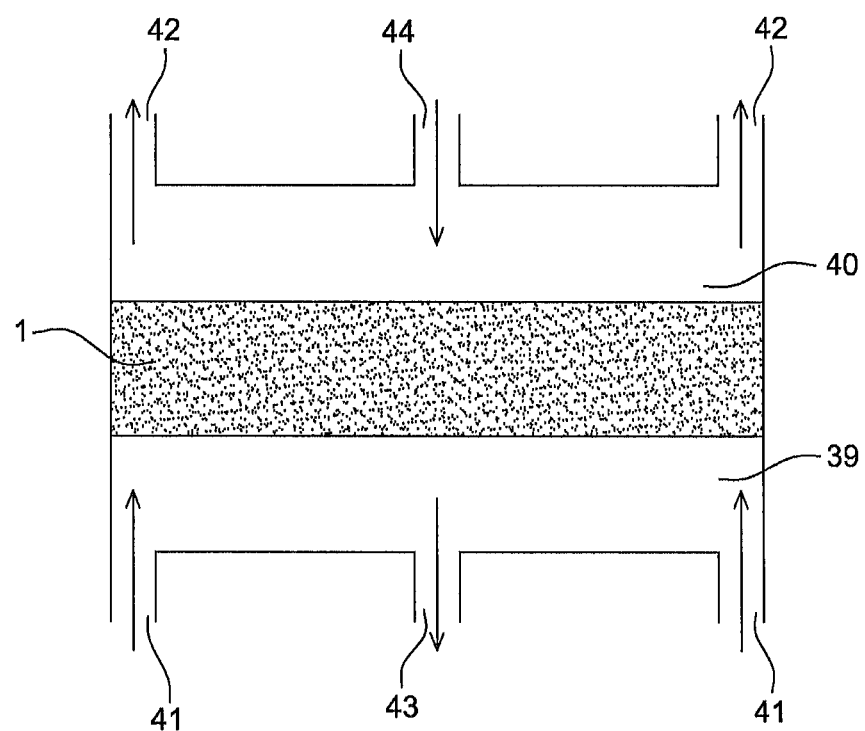

For example, membranes of a non-parallelepiped shape may be used. For example, FIGS. 9 and 10 represent a device implementing the invention, in which membrane 1 presents a cylindrical longitudinal section. In this embodiment, the first compartment 39 and the second compartment 40 extend on either side of the membrane. The first compartment presents a longitudinal section of cylindrical form, like the second compartment. The first compartment 39 comprises an entrance in ring form 41 (cross sectional view) and an exit 43. The entrances of the first compartment are situated on the periphery of the first compartment. The exit 43 of the first compartment is situated at the level of the centre of the first compartment. The second compartment comprises an entrance 44 situated facing the exit 43 of the first compartment, and an exit in ring form 42, each situated facing one of the entrances 41 of the first compartment. As with the previous embodiment, the fluxes of hydrated gas therefore traverse the two compartments in the opposite direction from each other.

The invention claimed is:

1. A method of determining the electroosmotic transport coefficient of a proton exchange membrane, the membrane being disposed between a first compartment and a second compartment, the first and second compartments each extending on either side of the membrane, the first and second compartments each presenting an entrance and an exit, the entrance of the first compartment being situated facing the exit of the second compartment and the entrance of the second compartment being situated facing the exit of the first compartment, the method comprising:

(i) providing a flux of hydrated gas in each of the compartments, the flux of hydrated gas in the first compartment being a flux of hydrated hydrogen, the flux of hydrated gas being directed, in each of the compartments, from the entrance to the exit, the flux of hydrated gas, in each of the compartments, being controlled such that, in continuous operation, a relative humidity in the entrance of at least one of the compartments is equal to a relative humidity in the exit of the other of the compartments;

(ii) providing a proton current through the membrane of the first compartment in the direction of the second compartment, (iii) determining a total flux of water that crosses the membrane, in continuous operation, from the first compartment in the direction of the second compartment by using at least one measurement of the quantity of water at the exit of the second compartment, (iv) calculating the electroosmotic transport coefficient from the total water flux.

2. The method according to claim 1, wherein the flux of hydrated gas in each of the compartments is controlled so that, in continuous operation, the relative humidity remains substantially the same between the entrance and the exit of each compartment.

3. The method according to claim 2, wherein the flux of hydrated gas that traverses each of the compartments is between 10 times and 2000 times greater than the flux of protons and water that traverses the membrane.

4. The method according to claim 1, wherein (i) comprises:
providing a single flux of hydrated hydrogen at the entrance of one of the compartments such that the single flux of hydrogen traverses the compartment,
recovering the single flux of hydrated hydrogen at the exit of the compartment,
providing the single flux of hydrated hydrogen recovered to the entrance of the other of the compartments.

5. The method according to claim 4, wherein a measurement of the quantity of water at the exit of the second compartment is a measurement of the relative humidity at the exit of the second compartment.

6. The determination method according to claim 1, wherein (i) comprises:
providing a flux of hydrated hydrogen to the entrance of the first compartment so that the relative humidity at the entrance of the first compartment is equal to the relative humidity at the exit of the second compartment;
providing a flux of hydrated gas to the entrance of the second compartment so that the relative humidity at the entrance of the second compartment is equal to the relative humidity at the exit of the first compartment.

7. The method according to the previous claim 6, wherein a measurement of the quantity of water at the exit of the second compartment is a measurement of the water weight at the exit of the second compartment.

8. The method according to claim 1, wherein (iii) comprises:
calculating the water flux provided at the entrance of one of the compartments
measuring the relative humidity at the exit of the compartment,
calculating the water flux at the exit of this the compartment
calculating the total water flux having traversed the membrane by calculating a difference between the water flux at the entrance and exit of this compartment.

9. The method according to claim 1, wherein, during (iv), the total water flux is referred to as an electroosmosis flux.

10. The method according to claim 1, wherein (iv) comprises:

(v) calculating a back diffusion flux that traverses the membrane from the second compartment to the first compartment;

(vi) a step of calculating the electroosmosis flux from the sum of the total water flux and the back diffusion water flux.

11. The method according to claim 10, wherein (iv) comprises:

stopping the proton current through the membrane;

recording a curve representative of the variation in relative humidity at the exit of the second compartment as a function of time calculating a curve representative of the variation in water flux at the exit of the second compartment as a function of time;

calculating the back diffusion flux by interpolating the curve representative of the variation in water flux at the exit of the second compartment as a function of time.

12. The method according to claim 11, wherein calculating the back diffusion flux by interpolation comprises:

determining a function of the form $\lambda_1 e^{-t/\tau_1} + \lambda_2 e^{-t/\tau_2} + \lambda_3$ that is most similar to the curve representative of the variation in water flux at the exit of the second compartment as a function of time;

identifying the back diffusion flux with the coefficient $\lambda_1$ or $\lambda_2$ associated with the highest time constant t1 or t2.

13. The method according to claim 3, wherein the flux of hydrated gas is substantially equal to 1000 times the flux of protons that traverses the membrane.

14. A device for determining the electroosmotic transport coefficient of a proton exchange membrane, the device comprising:

a first and a second compartment extending on either side of the membrane, the first and the second compartments each comprising an entrance and an exit, the entrance of the first compartment being situated opposite from the exit of the second compartment and the entrance of the second compartment being situated facing the exit of the first compartment, at least one hydrated gas supply configured to Provide a flux of hydrated hydrogen to the entrance of the first compartment and a flux of hydrated gas to the entrance of the second compartment, a power supply configured to provide a proton current across the membrane from the first compartment to the second compartment, a detector configured to measure the quantity of water at the exit of the second compartment, a controller configured to control the flow rate of the hydrated gas supply at the entrance of the second compartment, a computer configured to implement the steps of the method according to claim 1.

15. The device according to claim 14, comprising a looping system that connects the exit of the second compartment to the entrance of the first compartment.

16. The device according to claim 14, wherein the membrane extends along a longitudinal direction.

\* \* \* \* \*